United States Patent
Tortelli et al.

(10) Patent No.: US 7,795,477 B2
(45) Date of Patent: Sep. 14, 2010

(54) PROCESS FOR PREPARING FLUOROHALOGENETHERS

(75) Inventors: Vito Tortelli, Milan (IT); Pierangelo Calini, Milan (IT); Alberto Zompatori, Milan (IT); Emanuela Antenucci, Varese (IT)

(73) Assignee: Solvay Solexis S.p.A., Milan (IT)

(*) Notice: Subject to any disclaimer, the term of this patent is extended or adjusted under 35 U.S.C. 154(b) by 111 days.

(21) Appl. No.: 11/636,509

(22) Filed: Dec. 11, 2006

(65) Prior Publication Data
US 2007/0203368 A1    Aug. 30, 2007

(30) Foreign Application Priority Data
Dec. 22, 2005   (IT)   .......................... MI2005A2456

(51) Int. Cl.
C07C 41/22   (2006.01)
(52) U.S. Cl. ...................................... 568/685; 568/692
(58) Field of Classification Search .................... None
See application file for complete search history.

(56) References Cited

U.S. PATENT DOCUMENTS

| | | | |
|---|---|---|---|
| 3,450,684 A | 6/1969 | Darby | |
| 3,817,960 A | 6/1974 | Resnick | |
| 3,896,179 A | 7/1975 | Resnick | |
| 4,340,750 A | 7/1982 | Yamabe et al. | |
| 4,418,232 A * | 11/1983 | Maurin, III | 570/228 |
| 4,515,989 A | 5/1985 | Ezzell et al. | |
| 4,754,085 A * | 6/1988 | Gervasutti et al. | 570/175 |
| 4,827,024 A | 5/1989 | Guglielmo et al. | |
| 4,900,872 A | 2/1990 | Guglielmo et al. | |
| 5,350,497 A | 9/1994 | Hung et al. | |
| 6,255,536 B1 | 7/2001 | Worm et al. | |

FOREIGN PATENT DOCUMENTS

| | | |
|---|---|---|
| EP | 0 201 871 | 11/1986 |
| EP | 1 352 892 A1 | 10/2003 |

OTHER PUBLICATIONS

Florine Chem.: "*A Comprehensive Treatment*", Kirk Othmer Encyclopedia, pp. 242-259, 1995.

Barbour et al., "*The Preparation of Organic Fluorine Compounds by Halogen Exchange*", Adv. Fluorine Chem., 3, 1963, pp. 194-201.
Vecchio et al., "*Studies on a Vapour-Phase Process for the Manufacture of Chlorofluoroethanes*," J. Fluorine Chem. 4, 1974, pp. 117-139.
Weyl, vol. E10 B2, pp. 125-161, 2000.
Houben-Weyl: "Methods of Organic Chemistry: Organo-Fluorine Compounds"; George Thieme Verlag, Stuttgart, XP002432208, vol. E10b/part1, 1999, p. 317; part2, 2000, p. 134.

\* cited by examiner

*Primary Examiner*—Rosalynd Keys
(74) *Attorney, Agent, or Firm*—Arent Fox LLP

(57) ABSTRACT

A process for preparing perfluorovinylethers having general formula:

$$R_fO\text{---}CF\text{=}CF_2 \quad (IA)$$

where $R_f$ is a $C_1$-$C_3$ alkyl perfluorinated substituent, comprises the steps of:

1a) fluorinating olefins of formula:

$$CY''Y\text{=}CY'Cl \quad (II)$$

where Y, Y' and Y", equal to or different from each other, are H, Cl, Br, and are not contemporaneously hydrogen; and obtaining fluorohalogencarbons of formula:

$$FCY''Y\text{---}CY'ClF \quad (III)$$

where Y, Y' and Y" are as above;

2a) dehalogenating or dehydrohalogenating fluorohalogencarbons (III) and obtaining fluorohalogenolefins of formula:

$$FCY_I\text{=}CY_{II}F \quad (IV)$$

where $Y_I$ and $Y_{II}$, equal to or different from each other, are H, Cl, Br and are not contemporaneously H;

3a) reacting a hypofluorite of formula $R_fOF$ and a fluorohalogenolefin (IV), and obtaining the fluorohalogenethers of formula:

$$R_fO\text{---}CFY_I\text{---}CF_2Y_{II} \quad (I)$$

where $Y_I$, $Y_{II}$, equal to or different from each other, are Cl, Br, H and are not be contemporaneously H; and 4a) dehalogenating or dehydrohalogenating compounds (I) and obtaining perfluorovinylethers (IA).

23 Claims, No Drawings

PROCESS FOR PREPARING FLUOROHALOGENETHERS

The present invention relates to a process for preparing fluorohalogenethers. More specifically the invention relates to fluorohalogenethers which by dehalogenation or dehydrohalogenation allow to obtain perfluorovinylethers. Still more specifically the present invention relates to a process for preparing perfluorovinylethers, preferably perfluoromethylvinylether, perfluoroethylvinylether and perfluoropropylvinylether, with improved yields and selectivity, and using precursors not belonging to the chlorofluorocarbon (CFC) class and besides obtainable without expensive separation processes from hydrogenated by-products.

As known, perfluorovinylethers are useful monomers for preparing various polymers, from fluorinated elastomers to fluorinated thermoprocessable semicrystalline polymers.

Processes for preparing perfluorovinylethers are known in the prior art. U.S. Pat. No. 3,450,684 relates to vinylethers of formula:

$$CF_2=CFO(CF_2CFX^0{}_fO)_{nI}CF_2CF_2X^0{}_I$$

wherein $X^0{}_I$=F, Cl, $CF_3$, H and nI can range from 1 to 20.

These compounds are obtained by starting from HFPO. The process is carried out in more steps according to the following scheme:

$$X^0{}_ICF_2CF_2O-(CFX^0{}_fCF_2O)_{nI-1}-CFX^0{}_fCOF + HFPO \dashrightarrow$$
$$X^0{}_ICF_2CF_2O-(CFX^0{}_fCF_2O)_{nI}-CF(CF_3)COF$$
$$X^0{}_fCF_2CF_2O-(CFX^0{}_fCF_2O)_{nI}-CF(CF_3)COF + NaOH \dashrightarrow$$
$$X^0{}_fCF_2CF_2O-(CFX^0{}_fCF_2O)_{nI}-CF(CF_3)COONa$$
$$X^0{}_ICF_2CF_2O-(CFX^0{}_fCF_2O)_{nI}-CF(CF_3)COONa \xrightarrow{212°C.}$$
$$X^0{}_fCF_2CF_2O-(CFX^0{}_fCF_2O)_{nI}-CF=CF_2$$

The yields of this process are low.

U.S. Pat. No. 3,817,960 relates to the preparation of perfluorovinylethers of formula:

$$CF_3O(CF_2O)_{n''}CF_2CF_2OCF=CF_2$$

wherein n'' can range from 1 to 5.

The synthesis requires the preparation of an acylfluoride of formula:

$$CF_3O(CF_2O)_{n''}CF_2C(O)F$$

by TFE oxidation at low temperature in the presence of U.V. radiations or by electrochemical fluorination of the corresponding hydrogenated acylfluoride. Then the acylfluoride is reacted according to the following scheme:

$$CF_3O(CF_2O)_{n''}CF_2C(O)F + HFPO \xrightarrow[Solv.]{CsF}$$
$$CF_3O(CF_2O)_{n''}CF_2CF_2OCF(CF_3)COF$$
$$CF_3O(CF_2O)_{n''}CF_2CF_2OCF(CF_3)COF \xrightarrow[Solvent]{Na_2CO_3}$$
$$CF_3O(CF_2O)_{n''}CF_2CF_2OCF=CF_2$$

In this synthesis scheme the preparation of the starting acylfluoride from TFE is an expensive process from the industrial point of view. When the electrochemical fluorination is used, the yields are low due to the formation of by-products.

U.S. Pat. No. 3,896,179 relates to the separation of perfluorovinylethers having a linear alkyl chain from branched alkyl chain isomer perfluorovinylethers by thermal decomposition at temperatures in the range 300°-600° C. As a matter of fact branched isomers generally act as chain transfer agents giving polymers having poor mechanical properties. Therefore branched vinylethers are undesired when linear vinylethers are used for obtaining polymers.

U.S. Pat. No. 4,340,750 relates to the preparation of perfluorovinylethers of formula:

$$CF_2=CFOCF_2R^0{}_fX^1$$

wherein $R^0{}_f$ is a $C_1$-$C_{20}$ perfluoroalkyl optionally containing oxygen, $X^1$=H, Cl, Br, F, COOR$^0$, CONR$^0$R' wherein R$^0$ is a $C_1$-$C_{10}$ alkyl group and R' represents H or a $C_1$-$C_{10}$ alkyl group. In the preparation of these compounds an acylfluoride together with iodine and tetrafluoroethylene is used. In this process the final step of the alkaline acylfluoride pyrolysis is avoided. The synthesis scheme is the following:

$$X^1R^0{}_fCOF + C_2F_4 + I_2 + KF \xrightarrow{Solvent} X^1R^0{}_fCF_2OCF_2CF_2I$$
$$X^1R^0{}_fCF_2OCF_2CF_2I \xrightarrow[Solvent]{Zn} X^1R^0{}_fCF_2OCF=CF_2$$

The drawback of this process is that the deiodofluorination reaction (last step of the reaction) takes place with low yields.

U.S. Pat. No. 4,515,989 relates to the preparation of new compounds for the fluorovinylether synthesis. According to the patent the vinylether synthesis is improved by using a specific compound capable to decarboxylate easily. For the intermediate preparation fluoroepoxides are used, of formula:

$$X^3CF_2-CF-CF_2 \atop \diagdown O \diagup \qquad (1a)$$

wherein $X^3$ = Cl, Br

The reaction scheme is the following:

$$R_{fA}COF + X^3CF_2-CF-CF_2 \xrightarrow{CsF} R_{fA}CF_2OCF(CF_2X^3)COF$$
$$R_{fA}CF_2OCF(CF_2X^3)COF \xrightarrow[120°C.]{Na_2CO_3/Solvent} R_{fA}CF_2OCF=CF_2$$

The drawback of this process is that the precursors for obtaining the fluoroepoxides (1a) are industrially hardly available.

U.S. Pat. No. 5,350,497 relates to the preparation of perfluoroalkylvinylethers through the fluorination with fluorine of partially fluorinated hydrodichloroethers and subsequent dechlorination, according to the following scheme:

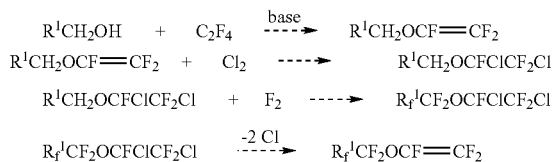

This process has the drawback that the fluorination step with fluorine takes place with not high yields and an excess of fluorine is employed to replace all the hydrogen atoms.

U.S. Pat. No. 6,255,536 describes a process wherein it is taken into account the synthesis of a hydrogenated precursor, which can also be partially halogenated, the precursor fluorination to form an acid derivative, which by alkaline pyrolysis is decomposed to perfluorovinylether. The scheme is the following:

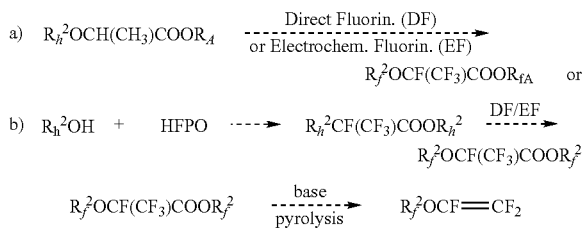

The fluorination step can be carried out by electrochemical fluorination or by fluorination with fluorine according to U.S. Pat. No. 5,488,142. The former reaction generally takes place with low selectivity and formation of undesired by-products. In the fluorination with fluorine industrially acceptable yields and productivity are not obtained. One operates indeed at high dilutions of the hydrogenated precursor and of the fluorine to control the heat produced by the reaction. Furthermore the fluorination with fluorine requires long reaction times, necessary for obtaining a complete fluorination of the compound. It is known that the fluorination of hydrogenated compounds is a very exothermic reaction which can cause the breaking of carbon-carbon bonds with formation of undesired by-products. See the book Fluorine Chemistry; A Comprehensive Treatment, in Kirk Othmer Encyclopedia, pages 242-259. Furthermore, to obtain a complete conversion, therefore to substitute all the hydrogen atoms of the precursor molecule, it is necessary to increase the temperature and therefore to adopt more drastic reaction conditions. This usually brings to a yield lowering in the useful product as there are secondary decomposition reactions.

EP 1,352,892 describes a process for preparing fluorinated vinylethers from acylfluorides, obtained by decomposition of fluorinated esters. The scheme is the following:

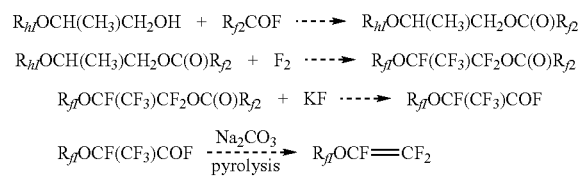

In the second step of the synthesis scheme the complete fluorination of the partially hydrogenated precursor esters is achieved obtaining the corresponding perfluorinated esters. This step of the complete fluorination of the partially fluorinated ester requires that the reaction is carried out for very long times, with several additions of a hydrogenated compound, for example benzene, to favour the total conversion of the ester. Contemporaneously the reaction temperature must be increased, for example from −10° C. up to room temperature. The productivity of this kind of fluorination is very low.

Processes for preparing fluorohalogen ethers by reacting hypofluorites with halofluorinated olefins are known in the prior art. U.S. Pat. No. 4,900,872 describes the synthesis of fluorohalogenethers by reaction between perfluoroalkyl hypofluorites, diluted in an inert solvent, and a halofluorinated olefin having formula $CA^I F{=}CA^{II} F$ wherein $A^I$ and $A^{II}$, equal to or different from each other, are Cl and Br. The olefin used in the syntheses described in the Examples of this patent is 1,2-dichloro-1,2-difluoroethylene (CFC 1112). The synthesis of said olefin is generally carried out by dehalogenation of the tetrachloro difluoroethane $CCl_2FCCl_2F$ (CFC 112) with metallic zinc in alcoholic solvent. See for example Houben Weyl, vol. E 10 B2, pages 125-161. The CFC 112 precursor used in this synthesis is a chlorofluorocarbon which, as said, falls within the Montreal protocols and its amendments on the reduction of the gas emissions destroying the ozone layer in the stratosphere. According to these protocols the CFC emissions must be gradually reduced in the time until they are then completely eliminated. Industrially CFC 112 was obtained as a component of a mixture of various chlorofluoroethanes, symmetric and asymmetric, mainly CFC 113 ($CF_2Cl{-}CFCl_2$) and CFC 114 ($CF_2Cl{-}CF_2Cl$).

The latter compounds were those of greater industrial interest as used as refrigerants and solvents. The synthesis methods of these chlorofluoroethane mixtures are for example reported in Adv. Fluorine Chem. 3 (1963), "The Preparation of Organic Fluorine Compounds by Halogen Exchange" pages 194-201, Fluorine Chem. 4 (1974), 117-139. Since it is no longer possible to use the CFC 113 and 114 compounds, also CFC 112 and thus CFC 1112 are industrially no longer available.

Furthermore, as said, CFC 112 was obtained in admixture with CFC 112a. The latter product formed in high amounts, sometimes in percentages higher than those of the symmetric CFC 112. See J. Fluorine Chem. 4 (1974), 117-139. CFC 112 and 112a have very close boiling points, respectively 92.8 and 91.5° C. They are thus hardly separable from each other by fractional distillation. Therefore, if one desires to obtain CFC 112 as pure as possible, there are low distillation yields, since the product is lost by drag together with CFC 112a. It is also to be noted that in the subsequent dechlorination to obtain CFC 1112, CFC 112a brings to the formation of CFC 1112a which, as well known, is a very toxic product. From the industrial point of view, CFC 112a must therefore be reduced to very low values, however, as said, this brings to very high losses in the target product CFC 112.

The need was felt to have available an industrial process for preparing fluorohalogenethers in high yields and selectivity, overcoming the drawbacks of the prior art.

The Applicant has surprisingly and unepectedly found a process overcoming the above technical problem.

An object of the present invention is a process for preparing perfluorovinylethers having general formula:

wherein $R_f$ is a $C_1$-$C_3$, preferably $C_1$-$C_2$, alkyl perfluorinated substituent;

comprising the following steps:

1a) Fluorination with Fluorine of Olefins having Formula:

$$CY''Y=CY'Cl \qquad (II)$$

wherein Y, Y' and Y", equal to or different from each other, are H, Cl, Br, with the proviso that Y, Y' and Y" are not contemporaneously hydrogen; and obtainment of fluorohalogencarbons of formula:

$$FCY''Y-CY'ClF \qquad (III)$$

wherein Y, Y' and Y" have the above meanings;

2a) dehalogenation or dehydrohalogenation of the fluorohalogencarbons of formula (III) with removal of molecules of halogen/hydrohalogenic acid wherein the halogen/halide ion is Cl or Br, and obtainment of fluorohalogen olefins of formula:

$$FCY_I=CY_{II}F \qquad (IV)$$

wherein $Y_I$ and $Y_{II}$, equal to or different from each other, have the meaning of H, Cl, Br with the proviso that $Y_I$ and $Y_{II}$ are not both H;

3a) reaction of the fluorohalogenolefin of formula (IV) with a hypofluorite of formula $R_fOF$, wherein $R_f$ is as above defined, obtaining the fluorohalogenethers of formula:

$$RfO-CFY_I-CF_2Y_{II} \qquad (I)$$

wherein:

$Y_I$, $Y_{II}$, equal to or different from each other, are Cl, Br, H with the proviso that $Y_I$ and $Y_{II}$ cannot be contemporaneously equal to H;

4a) dehalogenation or dehydrohalogenation of the compounds of formula (I) and obtainment of the perfluorovinylethers of formula (IA).

The Applicant has surprisingly and unexpectedly found that, with the process of the invention, it is possible to obtain in particular perfluoromethylvinylether, perfluoroethylvinylether in high yields and selectivity. Furthermore in the process of the invention, when the fluorohalogencarbon (III) is a symmetric organic compound, that is Y=Cl and Y'=Y", the impurity of the corresponding asymmetric isomer, when present, is in a very reduced amount, lower than 2%, preferably lower than 1%.

The amount of the asymmetric isomer when the fluorohalogencarbon (III) is a symmetric organic compound with the two carbon atoms having the same substituents of halogen type can be further lowered, before performing step 2a), by carrying out the following step:

5a) separation, preferably by distillation, of the residual asymmetric isomer from the symmetric fluorohalogencarbon of formula (III).

For example CFC 112, obtained in step 1a) (in formula (III) Y'=Cl, Y" and Y are both Cl), contains very reduced amounts of the asymmetric isomer 112a ($CCl_3$—$CClF_2$), and can be removed by fractional distillation.

It has been found that the separation yield, in particular the distillation yield, compared with the prior art processes results significantly improved.

In step 1a) the fluorination reaction takes place by addition of gaseous fluorine, optionally in the presence of an inert diluent as, for example, $N_2$, He, etc., to the olefins of formula (II), liquid at the reaction temperature. In step 1a) a solvent or a mixture of inert solvents can optionally be used, in the liquid state and miscible among each other under the conditions in which this step is carried out.

Step 1a) generally is carried out at temperatures between −120° C. and +10° C., preferably −90° C. and −15° C.

The olefins of formula (II) are preferably selected from the following: tetrachloroetilene, trichloroethylene, 1,2-di-chloroethylene and 1,1-dichloroethylene.

In step 2a) the dehalogenation (chlorine or bromine removal) of fluorohalogencarbons (III) is, for example, carried out by reaction of said compounds with transition metals as zinc, copper, manganese or metal couples as Zn/Cu, Zn/Sn, Zn/Hg, in the presence of solvents as, for example, hydrogenated protics as, for instance, alcohols, or hydrogenated ethers as, for example, glymes, dioxane, or dipolar aprotic solvents such as, for example, DMF, DMSO.

In step 2a) the dehydrohalogenation (HCl or HBr removal) of the fluorohalogencarbons of formula (III) takes place, for example, by reacting these compounds with an inorganic base, preferably NaOH or KOH, or an organic base, preferably primary, secondary or tertiary alkyl or aryl amines. Liquid phase is generally used. The elimination reaction of hydrohalogenic acid in step 2a) can optionally be carried out in the presence of a solvent, preferably aqueous or alcoholic. By using aqueous inorganic bases the reaction can be carried out in the presence of a quaternary ammonium or phosphonium salt as ammonium or phosphonium tetrabutyl, preferably chloride, ammonium or phosphnium trioctyl benzyl, preferably chloride, etc. Alternatively, or in admixture with the quaternary ammonium or phosphonium salts, other salts, as, for example, sulphonium salts, can be used.

In the dehalogenation or dehydrohalogenation step 2a) generally one operates at temperatures in the range 0°-150° C., preferably 25°-100° C.

The compounds of formula (III) usable in step 2a) are preferably selected from the following: $CCl_2F$—$CCl_2F$, $CHClF$—$CHClF$, $CCl_2F$—$CHClF$, $CH_2F$—$CCl_2F$.

Step 3a) is carried out in liquid phase at temperatures between −130° C. and 0° C., preferably −100° C. and −40° C., by optionally using organic solvents, inert under the conditions of the reaction.

The perfluoroalkyl hypofluorites with number of carbon atoms equal to or higher than 2 are known from U.S. Pat. No. 4,827,024. The trifluoromethyl hypofluorite is known in the art.

Step 3a) can be carried out in various ways; for example in the reactor containing the olefin at the liquid state, optionally diluted with an inert solvent under the reaction conditions, the hypofluorite is fed, prepared in liquid or gaseous phase, diluted in a compound inert under the reaction conditions.

The compounds of formula (IV) usable in step 3a) are preferably CFCl=CFCl, CHF=CFCl.

The optional solvents usable in steps 1a) and 3a) are selected from the following: (per)fluoropolyethers, (per)fluoroalkanes, hydrofluorocarbons (HFC), hydrochlorofluorocarbons (HCFC), chlorofluorocarbons (CFC), perfluoroamines, hydrofluoroethers or hydrofluoropolyethers or mixtures thereof.

In the process of the present invention the ratio between the reactants in the various steps is not critical.

In step 4a) the dehalogenation or elimination of chlorine or bromine from fluorohalogen ethers of formula (I) is for example carried out by reaction of said compounds with transition metals as zinc, copper, manganese or metal couples as Zn/Cu, Zn/Sn, Zn/Hg, in the presence of solvents which can be either hydrogenated protics as alcohols, or hydrogenated ethers as glymes, dioxane, or dipolar aprotic solvents as DMF, DMSO.

In step 4a) the dehydrohalogenation or elimination of HCl or HBr from the fluorohalogenethers of formula (I) takes place, for example, by reacting these compounds with an inorganic base, preferably NaOH or KOH, or an organic base, preferably primary, secondary or tertiary alkyl or aryl amines. One generally operates in liquid phase. The elimination reaction of hydrohalogenic acid in step 4a) can optionally be carried out in the presence of a solvent, preferably aqueous or alcoholic. By using aqueous inorganic bases the reaction can be carried out in the presence of a quaternary ammonium or phosphonium salt as ammonium or phosphonium tetrabutyl, preferably chloride, ammonium or phosphnium trioctyl benzyl, preferably chloride, etc. Alternatively, or in admixture with quaternary ammonium or phosphonium salts, other salts as, for example, sulphonium salts, can be used.

In the dehalogenation or dehydrohalogenation step 4a) one generally operates at temperatures in the range 0°-150° C., preferably 25°-100° C.

In the process of the present invention the pressure is not critical and preferably one operates at atmospheric pressure.

The process of the present invention can be carried out in a discontinuous, semicontinuous or continuous way.

For example, with reference to step 1a) the semicontinuous process can be carried out by feeding gaseous fluorine and the olefin of formula (II) in the reactor containing the solvent or the mixture of the reaction solvents.

In step 3a) a continuous process can be used, wherein the gaseous hypofluorite and the compound of formula (III) are fed into the reactor, until reaching the steady state. In practice the reactants are fed into the reactor with known flow-rates, by continuously drawing the reaction mixture. The steady state is reached when the reactant and reaction product concentrations in the reactor are equal to the reactant and reaction product concentrations at the reactor outlet.

The fluorohalogenethers of formula (I), preparable with the process of the present invention, are for example the following: $CF_3O$—$CFCl$—$CF_2Cl$, $C_2F_5O$—$CFCl$—$CF_2Cl$, $C_3F_7O$—$CFCl$—$CF_2Cl$, $CF_3O$—$CFH$—$CF_2Cl$, $C_2F_5O$—$CFH$—$CF_2Cl$, $C_3F_7O$—$CFH$—$CF_2Cl$.

The process of the present invention, as said, has a high yield combined with a high selectivity, as each single step has a high yield combined with a high selectivity in the reaction products.

The fluorohalogencarbons used in step 2a) are synthesized in step 1a) by a selective and a high yield process mainly bringing to only one compound of formula (III). As said, the asymmetric isomers, when present, are in a remarkably reduced amount in comparison with the processes used so far for preparing perfluorovinylethers.

With the process of the invention, if desired, it is possible to prepare also the perfluoropropylvinylether.

To sum up, in the process of the invention perfluoroalkyl hypofluorites and chlorinated and chlorofluorinated olefins are used, wherein in particular chlorofluorinated olefins have high purity and thus contain remarkably reduced amounts of toxic impurities. For example, when the starting olefin is CFC 1112, the amount of CFC 1112a is very low, for example lower than 2% by weight, preferably lower than 1% by weight. Therefore the process of the invention allows to produce CFC 112 containing very low amounts of CFC 112a, so as to obtain the olefin CFC 1112 in high purity and reduced amounts of CFC 1112a.

The following Examples illustrate with non limitative purposes the invention.

EXAMPLES

Example A

Synthesis of $CF_3OF$ 10 l/h of gaseous fluorine, 5 l/h of CO and 10 l/h of nitrogen are contemeporaneously allowed to flow in an AISI 316 steel pipe (inner diameter 2.17 mm and length 100 mm). The reaction is triggered by heating the gas mixing zone at 100° C. for some minutes. During the whole time the reactor is cooled by air circulation so that the temperture is lower than 300° C.; at the reactor outlet the temperature is 250° C. Under these conditions CO and $F_2$ are converted into $COF_2$ with a yield higher than 95% (determined by IR analysis of the outflowing gaseous mixture).

The gaseous mixture, after cooling at 100° C., is allowed to flow through a catalytic bed formed of 300 g of fine milled anhydrous CsF having particle size lower than or equal to 0.1 mm, mixed with 300 g of needle-shaped copper having diameter of 0.2 mm and length 6-7 mm. The catalyst is placed in a tubular reactor (inner diameter 55 mm, length 250 mm). The reaction temperature among gases is maintained at 100° C. Under these conditions the $COF_2$ is converted into $CF_3OF$ with yield higher than 98%, determined by IR analysis of the outflowing mixture.

Example 1

Addition of Fluorine to Trichloroethylene

A solution formed of 25.5 g of trichloroethylene (TCE) and 475 g of $CF_3O$—$CFCl$—$CF_2Cl$ as reaction solvent is introduced into a 400 cc AISI 316 reactor, equipped with mechanical stirrer.

The solution is cooled, by a cryostat, at the temperature of −70° C. and under stirring one mole of fluorine diluted with nitrogen in a molar ratio 1/2 is fed through a bubbling inlet. Contemporaneously 1.07 moles of TCE are fed by a pump. The reactants are fed in 8 hours, maintaining the tem-perature at −70° C.

At the end of the reaction 633 g of solution are discharged, which are analyzed by GC/MS (gaschromatography coupled to the mass spectrometry). The TCE conversion is equal to 75% and the selectivity in CFC 122a ($CHClF$—$CCl_2F$) is 56.7%.

Example 2

Dehydrochlorination of CFC 122a ($CHClF$—$CCl_2F$) Obtained in the Example 1

90 g of CFC 122a obtained in the Example 1 having purity of 94%, 5 g of tetrabutylammonium hydroxide are introduced in a 250 ml four-necked reactor equipped with magnetic stirrer, dropping funnel, thermometer and water condenser. 26 g of NaOH in aqueous solution at 20% are added under stirring, containing the exothermic heat at 30° C. with a bath of $H_2O$ and ice. When the soda addition is ended, the mixture is left under stirring at 30° C. for additional 40 minutes. It is cooled to 10° C.: the final mixture shows two separate phases. The reaction mixture is poured in a separatory funnel maintained at the temperature of 10° C. 72 g of organic phase having a higher density, formed of the compound (65 g) CFC 1112 (FCCl=CClF), pure at 99%, are separated. Conversion 100%, yield 98%.

Example 3

Addition of $CF_3OF$ to CFC 1112 in a Discontinues Way 72.4 g of $CFCl_3$ as solvent and 5.3 g of CFC 1112 obtained in the Example 2 are introduced in a 50 cc glass reactor, equipped with mechanical stirrer, cooled at the temperature of −70° C. by cryogenic bath. Through a bubbling inlet 1.0 Nl/h of $CF_3OF$ diluted with nitrogen in molar ratio $N_2/CF_3OF$ of 1.6 are fed. The $CF_3OF$ addition is carried out for 10 minutes.

At the end of the reaction 82 g of mixture are discharged, which is analyzed by GC/MS. The CFC 1112 conversion is equal to 99%, the selectivity in $CF_3O$—CFCl—$CF_2Cl$ is 90%.

Example 4

Addition of $CF_3OF$ to CFC 1112 in a Semicontinuos Way

In the same reactor used in the Example 3, cooled at the temperature of −70° C. by cryogenic bath, 63.7 g of $CFCl_3$ are introduced. Through a bubbling inlet 2.0 Nl/h of $CF_3OF$ diluted with nitrogen in a molar ratio $N_2/CF_3OF$ equal to 1.6, and 6.2 g/h of CFC 1112, are fed. The $CF_3OF$ addition is carried out for 4 hours.

At the end of the reaction 110 g of mixture are discharged, which are analyzed by GC/MS. The CFC 1112 conversion is quantitative. The yield in $CF_3O$—CFCl—$CF_2Cl$ is 98.4%.

Example 5

Addition of Fluorine to Tetrachloroethylene (PCE)

50.9 g of $CF_3O$—CFCl—$CF_2Cl$ as reaction solvent are introduced in the same reactor used in the Example 3. The reactor is cooled, by a cryostat, at the temperature of −30° C. and by a bubbling inlet a PCE solution at 50% by weight of $CF_3O$—CFCl—$CF_2Cl$ solvent is fed, with a flow-rate of 5.04 g/h. Contemporaneously, through another bubbling inlet, 2.22 Nl/h of gaseous fluorine are fed. The fluorine is fed diluted with nitrogen in a molar ratio fluorine/nitrogen 1/2.

The reaction is carried out for 3 hours and the final solution analyzed by GC/MS. The PCE conversion is quantitative. The selectivity, expressed in % by moles, in $CCl_2F$—$CCl_2F$ (CFC 112) is 81%. The CFC 112a is present in the reaction mixture in a reduced amount (0.5% with respect to the CFC 112).

Example 6

Dechlorination of CFC 112 $CCl_2FCCl_2F$ Obtained in the Example 1.

60.0 g of zinc in powder, activated by washing with a HCl solution 3N, 500 ml of isopropanol, are introduced in inert nitrogen atmosphere in a 1 liter three-necked reactor, equipped with magnetic stirrer, dropping funnel, thermometer, connected by a vigreaux column and a water condenser to a cold trap maintained at the temperature of −75° C. The inner temperature is brought to 75° C. Then 114 g of $FCCl_2CCl_2F$ obtained as described in the Example 5 and then purified by fractional distilllation up to a purity of 99%, are dropwise added. When the addition is over, the mixture is left under stirring for one hour at 80° C. 67.9 g of CFC 1112 are collected in the cold trap. The yield in CFC 1112 is equal to 92%.

Example 7

Addition of $CF_3$—$CF_2$—$CF_2OF$ to CFC 1112

The hypofluorite $CF_3$—$CF_2$—$CF_2OF$ is synthesized according to the Example 8 of U.S. Pat. No. 4,827,024.

In the reactor used in the Example 1 and maintained at the temperature of −90° C., wherein 121.2 g of CFCl=CFCl (CFC 1112), obtained as from Example 2, and 452 g of $CF_2Cl$—$CF_3$ (CFC 115) as reaction solvent were previously introduced, 2.3 Nl/h of hypofluorite are fed. The reaction lasts 4 hours and the final solution is analyzed by GC/MS.

The selectivity in propyl adduct $CF_3$—$CF_2$—$CF_2O$—CFCl—$CF_2Cl$, referred to the fed hypofluorite, is 48.1%.

Example 8

Addition of $CF_3$—$CF_2OF$ to CFC 1112

The hypofluorite $CF_3$—$CF_2OF$ is synthesized according to the Example 1 of U.S. Pat. No. 4,827,024.

In a 150 ml AISI 316 reactor, equipped with mechanical stirrer and maintained thermostated at the temperature of −90° C., wherein 15.3 g of CFCl=CFCl (CFC 1112), obtained as from Example 2, and 100 g of $CF_2Cl$—$CF_3$ (CFC 115), were introduced, 2 Nl/h of hypofluorite are fed. The reaction is carried out for 3 hours and the final solution is analyzed by GC/MS.

The selectivity in ethyl adduct $CF_3$—$CF_2O$—CFCl—$CF_2Cl$, referred to the fed hypofluorite, is 79%.

The invention claimed is:

1. A process for preparing perfluorovinylethers having general formula:

$$R_fO—CF=CF_2 \quad (IA)$$

wherein $R_f$ is a $C_1$-$C_3$ alkyl perfluorinated substituent; comprising the following steps:
 1a) fluorination with fluorine of tetrachloroethylene and obtainment of $CCl_2F$—$CCl_2F$;
 2a) dehalogenation of $CCl_2F$—$CCl_2F$ wherein the halogen is Cl, and obtainment of FCCl=CClF;
 3a) reaction with a hypofluorite of formula $R_fOF$, wherein $R_f$ as above, of FCCl=CClF, obtaining the fluorohalogenethers of formula:

$$R_fO—CFCl—CF_2Cl \quad (I); \text{ and}$$

4a) dehalogenation of the compound of formula (I) and obtainment of the per-fluorovinylethers of formula (IA).

2. A process according to claim 1, wherein, when in the step 1a) the $CCl_2F$—$CCl_2F$ is a symmetric organic compound, the impurity of the asymmetric isomer is lowered by carrying out the step:
 5a) separation of the asymmetric isomer from the symmetric fluorohalogencarbon.

3. A process according to claim 1, wherein in step 1a) the fluorination reaction takes place by addition of gaseous fluorine, optionally in the presence of an inert diluent, to tetrachloroethylene liquid at the reaction temperature.

4. A process according to claim 3, wherein a solvent or a mixture of inert solvents and in the liquid state is used.

5. A process according to claim 1, wherein step 1a) is carried out at temperatures between −120° C. and +10° C.

6. A process according to claim 1, wherein in step 2a) the dehalogenation is carried out by reaction with transition metals or metal couples in the presence of hydrogenated protic or hydrogenated ether solvents, or dipolar aprotic solvents.

7. A process according to claim 1, wherein in step 2a) one operates at temperatures in the range 0°-150° C.

8. A process according to claim 1, wherein step 3a) is carried out in liquid phase at temperatures between −130° C. and 0° C., optionally in the presence of an organic solvent.

9. A process according to claim 1, wherein step 3a) is carried out by feeding in the reactor containing the olefin at the liquid state, optionally diluted with an solvent inert under the reaction conditions, the hypofluorite, prepared in liquid or gaseous phase, diluted in a compound inert under the reaction conditions.

10. A process according to claim 1, wherein in steps 1a) and 3a) solvents selected from the following are used: (per)fluoropolyethers, (per)fluoroalkanes, HFC, HCFC, CFC, perfluoroamines, hydrofluoroethers or hydrofluoropolyethers or mixtures thereof.

11. A process according to claim 1, wherein in step 4a) the dehalogenation is carried out by reaction with transition metals or metal couples in the presence of hydrogenated protic, hydrogenated ether solvents, or dipolar aprotic solvents.

12. A process according to claim 1, wherein in step 4a) one operates at temperatures in the range 0°-150° C.

13. A process according to claim 1, achievable in a discontinuous, semicontinuous or continuous way.

14. A process according to claim 1, wherein $R_f$ is a $C_1$-$C_2$ alkyl perfluorinated substituent.

15. A process according to claim 2, wherein said separation step is achieved by distillation.

16. A process according to claim 5, wherein step 1a) is carried out at temperatures between −90° C. and −15° C.

17. A process according to claim 6, wherein said transition metals are selected from the group consisting of zinc, copper, and manganese.

18. A process according to claim 6, wherein said metal couples are selected from the group consisting of Zn/Cu, Zn/Sn, and Zn/Hg.

19. A process according to claim 7, wherein step 2a) is performed at a temperature in the range of 25°-100° C.

20. A process according to claim 8, wherein step 3a) is carried out in liquid phase at temperatures between −100° C. and −40° C., optionally in the presence of an organic solvent.

21. A process according to claim 11, wherein said transition metals are selected from the group consisting of zinc, copper, and manganese.

22. A process according to claim 11, wherein said metal couples selected from the group consisting of Zn/Cu, Zn/Sn, Zn/Hg.

23. A process according to claim 12, wherein in step 4a) is performed at a temperature in the range of 25°-100° C.

* * * * *